(12) United States Patent
Fredenberg et al.

(10) Patent No.: US 10,561,378 B2
(45) Date of Patent: Feb. 18, 2020

(54) PRECISION AND RESOLUTION OF QUANTITATIVE IMAGING BY COMBINING SPECTRAL AND NON-SPECTRAL MATERIAL DECOMPOSITION

(71) Applicant: KONINKLIJKE PHILIPS N.V., Eindhoven (NL)

(72) Inventors: Jon Erik Fredenberg, Stockholm (SE); Karl Erik Lenason Berggren, Stockholm (SE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/097,631

(22) PCT Filed: May 31, 2017

(86) PCT No.: PCT/EP2017/063079
§ 371 (c)(1),
(2) Date: Oct. 30, 2018

(87) PCT Pub. No.: WO2017/211625
PCT Pub. Date: Dec. 14, 2017

(65) Prior Publication Data
US 2019/0159741 A1 May 30, 2019

(30) Foreign Application Priority Data

Jun. 7, 2016 (EP) ..................................... 16173360

(51) Int. Cl.
*A61B 6/03* (2006.01)
*A61B 6/00* (2006.01)
*G01N 23/044* (2018.01)
*G01N 23/083* (2018.01)
(Continued)

(52) U.S. Cl.
CPC ............ *A61B 6/032* (2013.01); *A61B 6/4241* (2013.01); *A61B 6/482* (2013.01); *A61B 6/484* (2013.01);
(Continued)

(58) Field of Classification Search
CPC ......... A61B 6/032; A61B 6/481; A61B 6/482; A61B 6/484; A61B 6/502; A61B 6/5217;
(Continued)

(56) References Cited

U.S. PATENT DOCUMENTS 5,020,085 A 5/1991 Kawara
7,668,289 B2 2/2010 Proksa
(Continued)

FOREIGN PATENT DOCUMENTS

WO 2013/076662 5/2013
WO 2014176328 10/2014
(Continued)

*Primary Examiner* — Thomas R Artman
(74) *Attorney, Agent, or Firm* — Larry Liberchuk (57) ABSTRACT

The invention proposes to combine spectral image data with non-spectral image data in order to overcome limitations of the different data taking methods. Results from the methods are preferably combined as functions of spatial frequency so that spectral image data provide high accuracy at low frequencies, whereas the non-spectral image data helps reducing the noise at high frequencies. The invention enables a range of applications in different fields of X-ray imaging such as improved tissue contrast and tissue characterization.

17 Claims, 2 Drawing Sheets

(51) Int. Cl.
*G01T 1/29* (2006.01)
*A61B 6/02* (2006.01)

(52) U.S. Cl.
CPC .......... *A61B 6/5205* (2013.01); *A61B 6/5235* (2013.01); *G01N 23/044* (2018.02); *G01N 23/083* (2013.01); *G01T 1/2985* (2013.01); *A61B 6/025* (2013.01); *A61B 6/502* (2013.01); *G01N 2223/3303* (2013.01); *G01N 2223/401* (2013.01); *G01N 2223/41* (2013.01); *G01N 2223/419* (2013.01); *G01N 2223/6126* (2013.01)

(58) Field of Classification Search
CPC ....... A61B 6/5229; A61B 6/5235; A61B 6/12; G01N 23/04; G01N 23/087; G01N 2223/401; G01N 2223/402; G01N 2223/405; G01N 2223/41; G01N 2223/423; G01N 2223/612; G01N 2223/6123; G06T 11/005; G06T 11/006
See application file for complete search history.

(56) References Cited

U.S. PATENT DOCUMENTS

| | | | |
|---|---|---|---|
| 8,639,003 B2* | 1/2014 | Bruder | G06T 5/002 382/131 |
| 8,755,585 B2* | 6/2014 | Nakanishi | A61B 6/032 382/131 |
| 2007/0147574 A1 | 6/2007 | Bernard | |
| 2011/0280459 A1* | 11/2011 | Nakanishi | A61B 6/032 382/131 |
| 2015/0178957 A1 | 6/2015 | Zou | |
| 2015/0348258 A1 | 12/2015 | Petschke | |
| 2016/0334520 A1* | 11/2016 | Flohr | G06T 11/008 |
| 2019/0159741 A1* | 5/2019 | Fredenberg | A61B 6/032 |

FOREIGN PATENT DOCUMENTS

| | | |
|---|---|---|
| WO | 2015/011587 | 1/2015 |
| WO | 2015/074916 | 5/2015 |

* cited by examiner

PRECISION AND RESOLUTION OF QUANTITATIVE IMAGING BY COMBINING SPECTRAL AND NON-SPECTRAL MATERIAL DECOMPOSITION

CROSS REFERENCE TO RELATED APPLICATIONS

This application is the U.S. National Phase application under 35 U.S.C. § 371 of International Application No. PCT/EP2017/063079 filed May 31, 2017, published as WO 2017/211625 on Dec. 14, 2017, which claims the benefit of European Patent Application Number 16173360.5 filed Jun. 7, 2016. These applications are hereby incorporated by reference herein.

FIELD OF THE INVENTION

The present invention relates to a calculation unit for processing quantitative image data, an X-ray imaging system, a method for quantitative image data processing, as well as to a computer program element and a computer readable medium.

BACKGROUND OF THE INVENTION

In clinical X-ray imaging, for instance in mammography, quantitative imaging is used to measure the amounts of different types of material, such as tissue, which may be used as input for improved risk assessment, detection, diagnosis, and treatment. For example, measurements of the volumetric breast density using quantitative imaging allows assessing the risk of developing breast cancer, assessing the efficiency of mammography, deriving improved radiation dose estimates, and monitoring the effect of drug treatment over time in order to adapt the drug dosage. Another application of quantitative imaging in mammography is to differentiate between different lesion types, for instance, cystic and solid lesions, in order to provide a better diagnosis.

Several methods for quantitative imaging are available, including spectral and non-spectral imaging methods. Spectral imaging refers to imaging an object at multiple photon-energy spectra, for example at least two different energy spectra. In WO 2013/076662, a method is described for spectral image processing in X-ray imaging. At a given dose, spectral imaging is generally associated with higher noise compared to non-spectral imaging because 1) the available dose is split over several spectra, and 2) the spectral processing often involves taking a difference between the different spectra, which is an operation that increases noise. The increased noise generally leads to a lower limit on the structure size, which can be detected and quantified. In contrast to spectral imaging, non-spectral quantitative imaging methods often rely on a-priori information and additional assumptions, or full non-spectral 3D image data such as acquired by computed tomography.

Quantitative imaging is often applied on a global level, reporting for instance a single value for an image or the entire breast. However, local quantitative information, for instance a map of material properties over a breast, can be valuable, for example to find regions of increased risk, for better differentiation in treatment monitoring, to classify or quantify local material properties, such as prevalence of certain materials, including tumor tissue, cyst fluid, and contrast medium. Local quantitative information obtained with spectral imaging may, however, be too noisy to be useful at reasonable dose levels. While quantitative information obtained with non-spectral imaging is less noisy at a given dose, the inherent need for assumptions and/or a-priori information often leads to lower overall precision of the measurement compared to spectral imaging.

US2007/147574A1 describes that a method for acquiring an image data set comprising energy integrating (EI) and energy discriminating (ED) data measurements is provided. The method comprises obtaining EI measurement data and ED measurement data during an acquisition cycle. The method then comprises combining the EI measurement data and the ED measurement data before, during or after reconstruction. Finally the method comprises performing reconstruction on the original or combined datasets to obtain one or more of an EI image and one or more ED component images.

WO2015/011587A1 describes that an imaging system includes a detector array that detects radiation traversing an examination region. The detector array includes at least a set of non-spectral detectors that detects a first sub-portion of the radiation traversing the examination region and generates first signals indicative thereof. The detector array further includes at least a set of spectral detectors that detects a second sub-portion of the radiation traversing the examination region and generates second signals indicative thereof. The imaging system further includes a reconstructor that processes the first and second signals, generating volumetric image data.

US2015/348258A1 describes that an apparatus is provided to reconstruct an image using combined third-generation energy-integrating computed tomography projection data and fourth-generation spectrally resolved computed tomography projection data. The apparatus includes processing circuitry configured to obtain first projection data representing projection data from an energy-integrating detector; obtain second projection data representing projection data from a photon-counting spectrally discriminating detector; and reconstruct a first combined-system basis image and a second combined-system basis image by solving a combined-system matrix equation using the first projection data and the second projection data.

SUMMARY OF THE INVENTION

Thus, there may be a need for providing enhanced quantitative image data on a local level, that is position-resolved quantitative information in an image.

The object of the present invention is solved by the subject-matter of the independent claims, wherein further embodiments are incorporated in the dependent claims and the following description.

It should be noted that the following described aspects of the invention apply for the calculation unit, the X-ray imaging system, the method as well as the computer program element and the computer-readable medium.

According to a first aspect of the present invention, a calculation unit for processing of quantitative image data is provided. The calculation unit comprises a receiving unit and a processing unit. The receiving unit is configured for receiving spectral image data of an object of interest. The receiving unit is further configured for receiving non-spectral image data of the object of interest. The processing unit is configured for calculating material properties as a function of position from the spectral image data. Similarly, the processing unit is configured to calculate material properties as a function of position from the non-spectral image data. Furthermore, the processing unit is configured for combining the material properties calculated from the spectral and from the non-spectral image data.

According to the first aspect of the present invention, the combination of material properties as a function of position is carried out by the processing unit by combining the material properties as a function of spatial frequency by weighting the spectral and the non-spectral image data depending on the spatial frequencies in the image.

According to one embodiment, by combining the material properties calculated from spectral and from non-spectral image data, the processing unit is configured to give stronger weights to the low-spatial-frequency parts of the spectral image data as compared to the low-spatial-frequency parts of the non-spectral image data. Accordingly, the processing unit may further be configured to give stronger weights to the high-spatial-frequency parts of the non-spectral image data as compared to the high-spatial-frequency parts of the spectral image data.

It is an idea of the invention to combine the information from different quantitative imaging methods, in particular from spectral and non-spectral imaging, in order to overcome the limitations of the different methods thereby obtaining enhanced resolution and precision and eventually improved information. In particular, high-spatial-frequency information obtained from, for instance tomosynthesis and/or non-spectral two-dimensional (2D) methods can be combined with the low-spatial-frequency information obtained from spectral imaging in order to create high-precision and low-noise data, which can be used for local quantitative imaging, for instance to create a map of material properties. In this way enhanced quantitative image data can be provided on a local level, that is position-resolved quantitative information in an image.

Spectral image data are acquired by imaging the object of interest at least at two different X-ray energy spectra, and utilizing the fact that the attenuation of different materials is composed of different combinations of interaction mechanisms with corresponding differing energy dependencies. As an example, the attenuation of soft tissue, such as breast tissue, is mainly composed of photoelectric absorption and Compton scattering, which in turn depend on the atomic number and the electron density of the tissue. By extracting the respective contributions to the total attenuation from these two components using their respective energy dependencies, the imaged tissue can be decomposed into two constituents such as adipose and fibro-glandular breast tissue. For example, spectral image data can be obtained from at least two X-ray images of the object of interest acquired by exposing the object to at least two different X-ray spectra thereby obtaining, for example, a high-energy and a low-energy spectral image.

According to a second aspect of the invention, an X-ray imaging system for providing enhanced quantitative image information is provided. The system comprises a calculation unit for processing quantitative image data according to the above described aspect and the above described embodiments. Further, the system comprises an imaging unit, which is configured for providing spectral and non-spectral image data to the calculation unit. The X-ray imaging apparatus may further comprise an X-ray source, an X-ray detector arrangement comprising the aforementioned imaging unit. The X-ray source is configured to provide X radiation towards the X-ray detector arrangement. The X-ray detector arrangement is configured to detect radiation with at least two different X-ray energy spectra in order to provide spectral image data. For instance, the X-ray source can be configured to provide radiation with a first fixed energy spectrum and the X-ray detector arrangement can be configured to detect the radiation after it has passed through an object of interest. The X-ray source can then be configured to subsequently provide radiation with a second fixed energy spectrum, differing from the first fixed energy spectrum, and the X-ray detector arrangement can be configured to detect signals corresponding to the second fixed energy spectrum, after the radiation has passed through the object of interest. Non-spectral image data can subsequently be derived, for instance, from the spectral image data in terms of a sum or integral over the spectral image data related to the at least two different X-ray energy spectra provided by the X-ray source. Non-spectral image data may also be provided separately. For instance, in order to provide non-spectral image data, the X-ray source can be configured to provide an additional spectrum of X rays and the X-ray detector arrangement can be configured to detect the radiation after it has passed through the object of interest.

According to an embodiment, the X-ray imaging system is configured to acquire phase contrast, differential phase contrast, or dark field images. In this case, the spectral and/or the non-spectral image data are phase contrast data, differential phase contrast data, or dark field data.

According to one embodiment, the spectral and/or the non-spectral image data contain information on the phase of the X rays that have passed through the object of interest instead of, or in addition to, information on the absorption of the X rays. Such information is referred to as phase contrast and can in some configurations be acquired as the differential of the phase with respect to position in the image, in which case it is referred to as differential phase contrast.

According to one embodiment, the spectral and/or the non-spectral image data contain information on the small-angle X-ray scattering properties of the object instead of, or in addition to, information on the absorption of the X rays. Such information can be used to form so-called dark-field images.

The acquisition of spectral and non-spectral image data may be done simultaneously, for instance with an energy-resolved photoncounting detector. In the latter case, spectral image data may refer to counts of photons at specific energy intervals, whereas the non-spectral image data may refer to the integrated, hence summed/overall, photon-count data. The acquisition of the spectral and non-spectral data can, however, also be done separately, for instance by two different X-ray imaging systems or two different X-ray imaging methods.

It should be noted that the present invention in particular refers to improvement of image data acquired as two-dimensional (2D) data and/or tomosynthesis data. Computed tomography (CT) imaging with full three-dimensional (3D) information is however not a scope of the present invention.

According to a third aspect of the present invention, a method for quantitative image data processing is provided. The method comprises the steps of acquiring spectral image data of an object of interest and a subsequent calculation of material properties as a function of position from the spectral image data. Further, non-spectral image data of the object of interest are acquired and material properties are calculated as a function of position from the non-spectral data. Eventually, the material properties calculated from the spectral and from the non-spectral data are combined as a function of spatial frequency.

It is understood that the steps of the method can also be performed in a different order. The non-spectral image data can be acquired before the spectral image data, or the spectral and the non-spectral image data can be acquired simultaneously. Further, the processing, i.e. the calculation of material properties as a function of position, of the spectral and the non-spectral image data can be done in a different order. For instance, the non-spectral image data can be processed before processing of the spectral image data, or processing of the spectral and the non-spectral image data can be one in parallel/simultaneously.

According to an embodiment, the material properties calculated from the spectral and the non-spectral image data are provided as a visual representation. A visual representation can, for instance, be given by a map of the object of interest showing the overall structure of the object of interest and depicting different (sub-) structures and/or materials in terms of different colors.

According to an embodiment, the spectral image data and/or the non-spectral image data are tomosynthesis data. Tomosynthesis is a technique that provides 3D information by imaging an object from a limited range of angles, as opposed to CT, which provides full 3D information by imaging the object from an angular range of at least 180 degrees. A tomosynthesis acquisition is often visualized as a stack of slices, which can be scrolled through. A consequence of the limited angular range in tomosynthesis is that the depth resolution becomes relatively poor as opposed to the in-plane resolution of the slices.

According to an embodiment, the non-spectral image data are acquired as a part of the acquisition of the spectral image data. In other words, the non-spectral image data are acquired during the acquisition of the spectral image data. That is, the non-spectral image data may be acquired as data derived from the spectral image data. This can be done using a photon-counting detector, with the non-spectral image data referring to the total counts of photons. However, image data acquisition is not limited to the use of photon-counting detectors. Other types of detectors can be used in order to acquire non-spectral data as part of spectral-data acquisition as well. Examples for other detectors are sandwich detectors, and examples for other imaging configurations are multiple exposures while switching kVp (peak kilo voltage, referring to the acceleration voltage of the X-ray tube) and/or X-ray filtration combined with a photon counting or an integrating detector.

According to an embodiment, the step of acquisition of the non-spectral image data comprises the use of additional a priori assumptions and/or additional data input. For example, shape models for the object of interest, a thickness measurement or known material properties in certain locations of the image can be used in this context. For example, in case of breast-density measurements, where breast density refers to the fractional amount of fibro-glandular tissue in the breast, the height of the compression paddle, possibly in combination with a breast shape model, can be used to normalize a non-spectral image thereby making it quantitative. Another option for providing a-priori information to non-spectral image data is to search for an area in the image, which contains only one type of material, for instance fatty breast tissue, and to use the pixel value in that area to normalize the image. It is also possible to use histogram information in the image to correlate pixel value to a certain physical aspect of the object that is being imaged.

According to an embodiment, the step of combining the material properties calculated from the spectral and the non-spectral image data as a function of spatial frequency is at least partly carried out in the spatial-frequency domain, for instance defined by the Fourier transform of the image.

According to another embodiment, the step of combining the material properties calculated from the spectral and the non-spectral image data as a function of spatial frequency is at least partly carried out in the spatial domain. This may comprise the step of a convolution with a filter kernel and/or by means of low-pass, band-pass or high-pass filtering.

According to the third aspect of the invention, the step of combining the material properties calculated from the spectral and from the non-spectral image data comprises the step of weighting of the respective data depending on the spatial frequencies of the image. In this step, a weighting function can be used, which gives stronger weight to the low-spatial-frequency parts of the spectral image data as compared to the low-spatial-frequency parts of the non-spectral image data. Additionally, the weighting function can give a stronger weight to the high-spatial-frequency parts of the non-spectral image data as compared to the high-spatial-frequency parts of the spectral image data.

The weighting function may be a linear weighting function.

In the step of calculation of material properties from the spectral and from the non-spectral data, properties identifying or characterizing a lesion, such as a cyst, a tumor or a microcalcification can be identified and/or quantified. Instead or in addition, properties identifying glandular and adipose breast tissue or skin may be identified and/or quantified, or a total volume or concentration of a contrast agent used in the object of interest when the image data are acquired may be identified and/or quantified.

According to a fourth aspect of the invention, a computer program element is disclosed, which is adapted to carry out the above and in the following described method steps.

According to a fifth aspect of the invention, a computer readable medium is disclosed, which comprises a program element according to the aforementioned aspect of the invention.

It may be seen as a gist of the invention to combine information from spectral image data and from non-spectral image data, thus providing enhanced precision and resolution in local imaging, in particular in clinical applications, such as mammography.

These and other aspects of the invention will become apparent from and will be elucidated with reference to embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
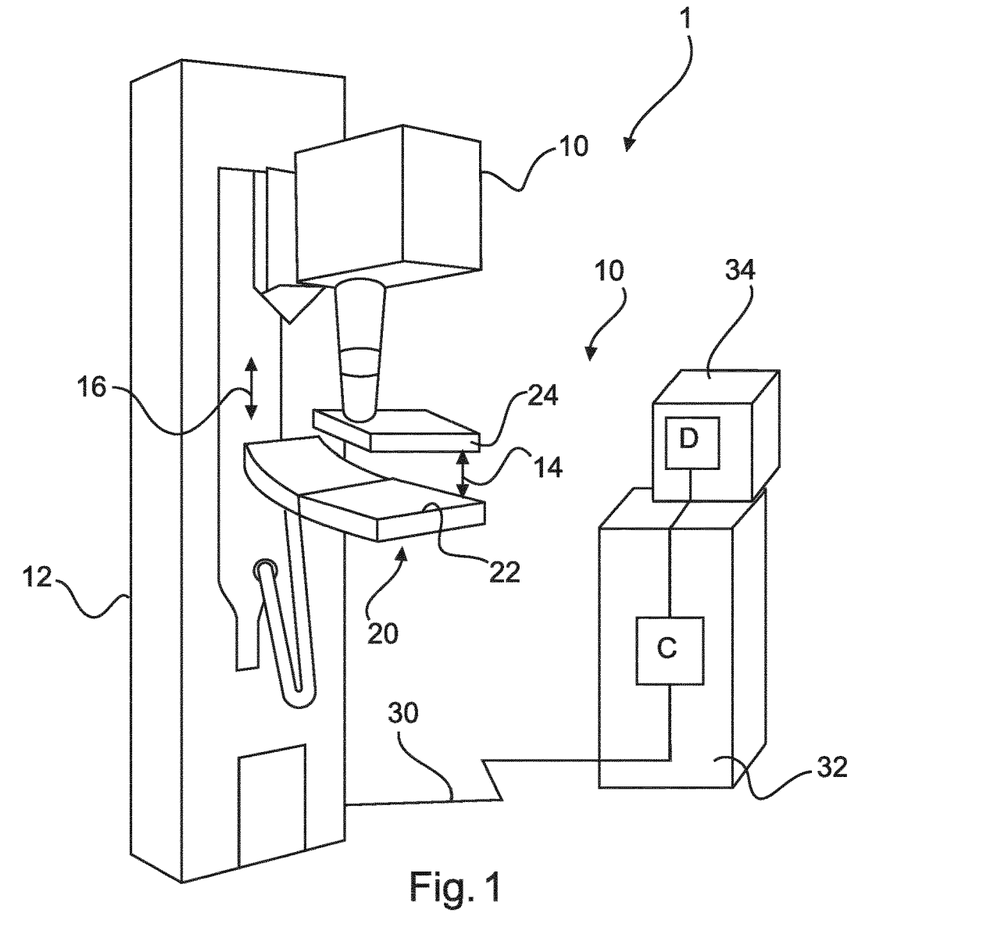
FIG. 1 shows an X-ray imaging system with a calculation unit according to an embodiment of the invention.

FIG. 1 shows an X-ray imaging system 1, which is given by a mammography system using, for instance, a photon counter. The X-ray imaging system 1 comprises an X-ray source 10 mounted on a vertical support structure 12.

Further, an X-ray detector arrangement 20 is mounted on the vertical support structure 12 comprising a first support surface 22, on which a patient can, for instance, arrange a breast onto. An adjustable compression plate, or compression paddle, 24 is arranged above the first support surface 22, allowing a breast to be arranged between the compression plate 24 and the first support surface 22. The compression plate is adjustable in height, as indicated by the double arrow 14, in order to adapt the distance between the first support surface and the breast touching surface of the compression plate. The X-ray detector arrangement may comprise an imaging unit, which is configured to provide spectral image data as well as non-spectral image data to a calculation unit of the X-ray imaging system, which is described hereinafter. Furthermore, the X-ray detector arrangement is adjustable in height, as indicated by the double arrow 16, so as to suitably adjust to the height of a patient.

The X-ray imaging system 1 further comprises data and supply connections 30. By means of these connections, raw image data acquired with the X-ray detector arrangement, in particular the imaging unit, can be provided to a calculation unit C, exemplarily comprised in a housing structure 32 in FIG. 1. It is noted that data and supply connections can be wired and/or wireless connections, as for example WLAN or Bluetooth connections. Further, image data can be stored on a computer readable medium such as a CD, DVD, portable flash drives or portable hard-disk drives, and can be provided to the calculation unit C by means of a suitable data provision unit, such as for instance a CD or DVD drive or a USB port connected to the calculation unit C.

The calculation unit C can be connected to a display unit D comprised in display housing structure 34, which is adjusted for visual representation of quantitative image data that have been processed by the calculation unit C. For instance, quantitative image data visualized by the display unit D can be maps of volumetric breast density, also referred to as glandularity maps, or maps of any other combination of materials, calculated from spectral and non-spectral image data, which have been acquired by the X-ray detector arrangement and which have been processed by the calculation unit C.

It is noted that the present invention is also related to other types of mammography X-ray imaging systems, for instance systems in which the patient is lying on a support structure with the face looking downwards, such as biopsy systems. Further, the X-ray imaging system may also comprise further movable structures to which the X-ray source and the X-ray detector arrangement can be mounted, for example the image may be acquired by scanning a narrow detector across the image field and/or the X-ray tube may be moved along an arc to obtain image data from multiple angles.

It is further noted that the present invention is not limited to mammography systems. The X-ray system can be any type of 2D or tomosynthesis X-ray imaging system that provides spectral and non-spectral image data.

The arrangement shown in FIG. 1 is schematic and exemplary. An X-ray imaging system according to the invention could, for instance, also have a common housing for the X-ray detector arrangement comprising the imaging unit, the calculation unit and the display unit.

Figure 2:
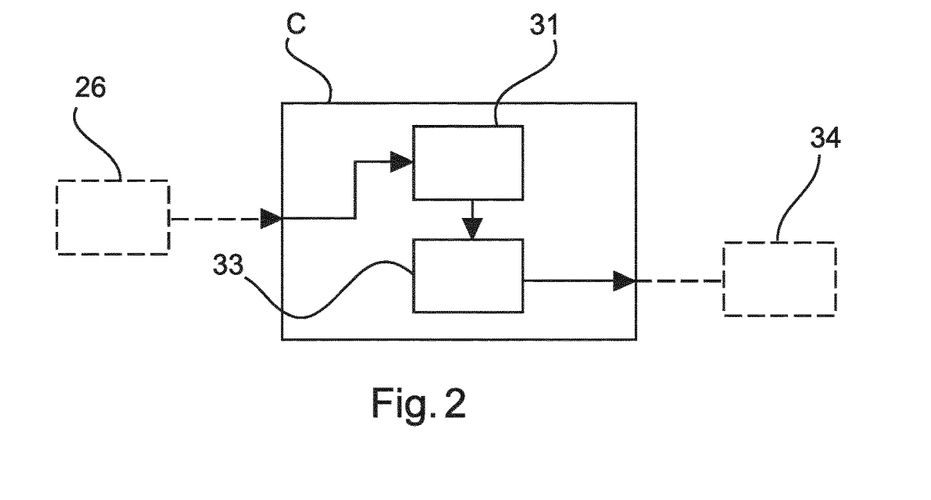
FIG. 2 shows a calculation unit according to an exemplary embodiment of the present invention.

FIG. 2 schematically shows a calculation unit C according to an exemplary embodiment of the invention. The calculation unit comprises a receiving unit 31 and a processing unit 33. The former receiving unit can be configured to receive spectral and non-spectral image data from an imaging unit 26. Thereby, the imaging unit 26 can be comprised in an X-ray detector arrangement as exemplarily shown in FIG. 1. The order in which the spectral image data and the non-spectral image data are received by the receiving unit 31 in FIG. 2 is arbitrary. Receiving may be successively or simultaneously. The receiving unit 31 can then supply the spectral and the non-spectral image data to the processing unit 33. It should be noted that the receiving unit 31 can also receive spectral and/or non-spectral image data, which have been acquired previously and are stored on a storage medium, which might be connected to the calculation unit for providing the respective image data to the receiving unit 31. The processing unit 33 calculates material properties as a function of position from the spectral image data and from the non-spectral image data. This can be done simultaneously or subsequently. The order in which calculation is performed by the processing unit is arbitrary. The processing unit 33 is further configured for combining the calculated material properties from the spectral and the non-spectral image data as a function of spatial frequency. The combined result can then be provided to a display unit 34. Optionally, the latter display unit 34 can be configured for displaying the combined result on the material properties as a function of spatial frequency.

In the following, basic steps of an exemplary method for processing quantitative image data are described with respect to FIG. 3. It should be noted that the X-ray detector arrangement together with the calculation unit C shown in FIG. 1 can be arranged for performing the method steps described in the following. The method comprises the following basic steps. In a first step 110, spectral image data of an object of interest are acquired. Thereby, the object of interest can be the breast or part of the breast of a patient. The spectral image data can be acquired by an X-ray detector arrangement comprising, for instance a photon-counting detector. The spectral image data can be acquired by multiple exposures of the object of interest at different X-ray energy spectra, obtained, for instance, by using multiple acceleration voltages in the X-ray tube and/or multiple filtrations. Alternatively, the spectral image data can be acquired by a single exposure using one X-ray spectrum and an energy-sensitive detector, which divides the detected photons into several bins according to their respective energy. It is also conceivable to combine these two approaches. i.e. using two different spectra and an energy sensitive detector to further enhance the spectral information. In a subsequent method step 112, material properties as a function of position are calculated from the spectral image data. The position can refer to position in physical space, for instance in 2D or 3D coordinates. A temporal dimension may be added optionally. Further, in method step 114, non-spectral image data of the object of interest are acquired. From these non-spectral image data, material properties as a function of position are calculated in step 116.

It should be noted that the spectral and/or the non-spectral image data may contain information on the phase of the X-rays that have passed through the object of interest instead of, or in addition to, information on the absorption of the X rays. Such phase-contrast information might be acquired as the differential of the phase with respect to position in the image. In the latter case it is referred to as differential phase contrast. It should be further noted that the spectral and/or the non-spectral image data may contain information on the small-angle X-ray scattering properties of the object instead of, or in addition to, information on the absorption of the X rays. Such information can be used to form dark-field images.

Acquisition of the spectral and non-spectral data may be in the reversed order or combined into a single step in which the non-spectral data is derived from the spectral data. In method step 118 the material properties calculated from the spectral and from the non-spectral image data are combined as a function of spatial frequency, where the spatial frequency in this sense represents structure size in the image; it is essentially a measure of how often sinusoidal components of the image repeat per unit of distance.

In optional method step 120, a visual representation of the material properties calculated from spectral and non-spectral image data is provided.

The spectral data acquired in step 110 can be acquired with a spectral photon-counting detector. In this case, the spectral detector generates, for example, low-energy (for instance lower half of spectrum) and high-energy (for instance upper half of spectrum) counts, thereby generating two image data sets in each image acquisition. The full-spectrum total (non-spectral) counts are simply the sum of the low- and high-energy counts. The low- and high-energy data sets each have a lower number of counts per pixel and therefore a higher quantum noise compared to the total-count data. The total-count data can then generate an image with maximal signal-to-noise ratio, whereas the low- and high-energy data each generate images with different average energies and a lower signal-to-noise ratio than the total-count image. The low- and high-energy count images can subsequently be combined to generate a spectral image. The spectral images obtained by this procedure will have increased noise compared to the total-count image because 1) the signal-to-noise ratio in each of the low- and high-energy count images is lower, and 2) the spectral processing is often equivalent to taking a difference between the two images, which is an operation that essentially adds the noise of the two images while the image signal is reduced.

According to an exemplary embodiment, the spectral data in method step 110 are acquired as spectral tomosynthesis data. Spectral tomosynthesis data can be acquired using a photon-counting detector, or, for instance sandwich detectors, kVp switching, filter switching, or multiple exposures.

The non-spectral data acquired in method step 114 can be data related to a non-spectral image acquired separately or the non-spectral image can be the total-count data acquired as part of the spectral image acquisition.

Figure 3:
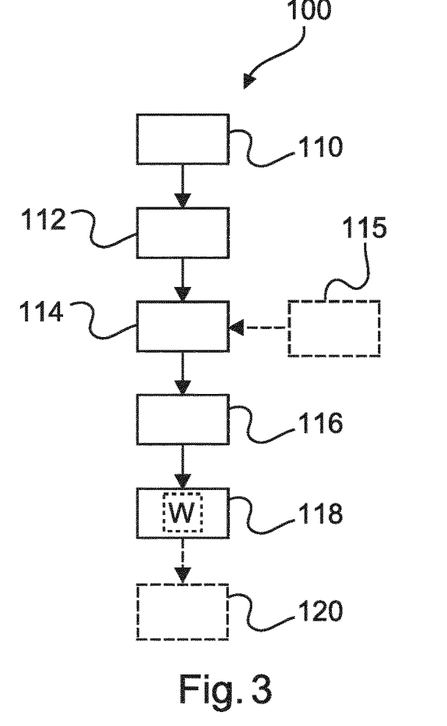
FIG. 3 shows basic steps of an exemplary method for enhanced quantitative image data processing according to an embodiment of the present invention.

The exemplary method according to FIG. 3 may include as further optional method step, the sub-step 115 of using additional a-prior assumptions and/or additional data input in the acquisition of the non-spectral image data. For example, the non-spectral image data may or may not be normalized using input from external sensors, for instance, an independent thickness measurement of the breast such as the compression height associated with the position of the compression paddle or the thickness and/or shape of the breast determined by optical or other sensors. Other external sensors that may provide additional information to normalize the non-spectral image data include sensors related to the compression force, pressure sensors on the compression paddle or the breast support, or any non-X-ray radiation sensors such as ultrasound sensors, optical sensors, radio-wave sensors, or radar sensors. Further, the non-spectral image data may or may not be subject to image processing operations including detection of a homogeneous area, breast height models, histogram analysis, segmentation or clustering operations, or any other operation with the purpose of converting the pixel values to a physical property of the imaged object.

According to one embodiment, the non-spectral data in step 114 can be tomosynthesis data. In tomosynthesis, differentiation between different tissue types can be accomplished in three dimensions (3D) by segmentation of the image pixel values on a slice-by-slice basis. Pixel-by-pixel two-dimensional (2D) tissue maps can be calculated by averaging in the depth direction. However, tomosynthesis provides only limited 3D information because the angular range of the acquisitions is limited and the in-plane resolution is generally much better than the depth resolution. Further, the depth resolution is better for structures with a small in-plane extent and is worse for large structures. Hence, the precision of the 3D segmentation will depend on the in-plane (2D) extension of the structure because of the asymmetric shape of the point-spread function. The segmentation will be good only for small structures, corresponding to high-spatial-frequencies. Large structures, corresponding to low-spatial-frequencies will be blurred in the depth direction and the contribution from these structures will be overestimated as they will occupy a larger number of slices than corresponding to their actual extent in the height direction. The limiting case is a structure that occupies the full in-plane field-of-view for which there will be no height information and which is not possible to segment in any of the slices.

The non-spectral image data acquired in step 114 can be tomosynthesis data acquired by a partial rotation with a C-arm CBCT (cone beam computed tomography) system. In this case, the spectral image data acquired in step 110 can be acquired, for instance, by multiple scans with alternating filters and/or kVp.

Material properties calculated from the spectral image data and material properties calculated from the non-spectral image data may include normal breast tissue, such as glandular and adipose breast tissue, and skin. Furthermore, material properties may include a contrast agent, such as iodine. In contrast-enhanced imaging the invention could, for instance, improve the measurement of iodine concentration by reducing noise. The invention could also improve visibility of iodine in the breast, enhancing the prevalence of iodine in blood vessels and smaller structures. In addition, or instead of the aforementioned material properties, material properties can include breast lesions, such as cysts, tumors, or micro calcifications.

Figure 4:
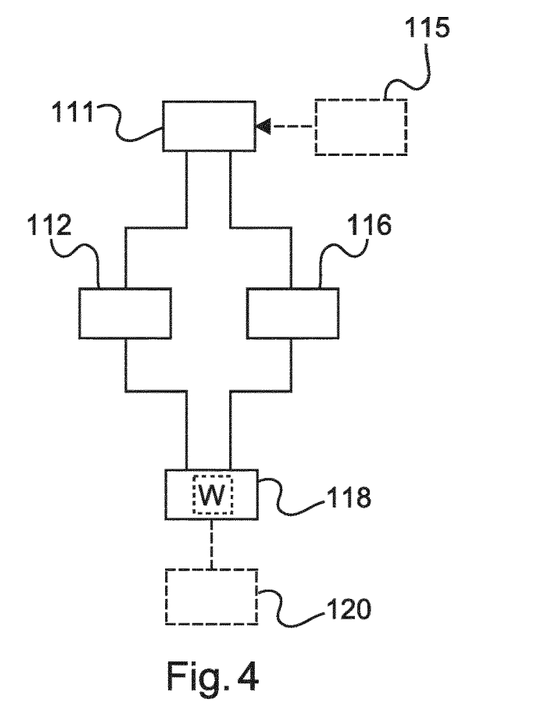
FIG. 4 shows a further example of a method according to an embodiment of the invention.

A further exemplary embodiment of a method according to the invention is shown in FIG. 4. FIG. 4 refers to the case where the non-spectral image data are acquired as part of the acquisition of the spectral image data in method step 111. As discussed in context of the method steps shown in FIG. 3, also in case of the exemplary embodiment shown in FIG. 4, the acquisition of the non-spectral data can comprise using additional a-priori information and/or additional data input, as indicated by method step 115. Examples are provided in context of the discussion of FIG. 3. From the spectral image data acquired in method step 111, material properties as a function of position are calculated in method step 112. As the non-spectral image data are acquired together with the spectral image data in step 111, the non-spectral data can be processed and material properties can be calculated from these data in method step 116. This method step, 116, can be performed in parallel, before or after method step 112. Eventually, the material properties calculated from the spectral image data in step 112 and calculated from the non-spectral image data in step 116 are combined in method step 118. As already discussed in context with FIG. 3 an optional method step 120 may follow to the method step 118 in FIG. 4. Optional method step 120 thereby refers to an adjustment of a visual representation of the combined material properties from the spectral and the non-spectral image data.

With reference to FIG. 3 and FIG. 4, the method step 118 can further comprise the following sub step, respectively. The method step 118 of combining the material properties calculated from the spectral and non-spectral image data may comprise the sub-step w of weighting the spectral and the non-spectral image data depending on the spatial frequency. The weighting can be done such that the low-spatial-frequency parts of the spectral image data get a stronger weight than the low-spatial-frequency parts of the non-spectral image data. Further, the weighting can give a stronger weight to the high-spatial-frequency parts of the non-spectral image data as compared to the high-spatial-frequency parts of the spectral image data. For instance, in an embodiment of the invention, weighting can be performed with a linear weighting function, which takes into account the aforementioned stronger weighting of spectral image data for low spatial frequencies and non-spectral image data for high spatial frequencies.

With further reference to method step 118 in FIG. 3 and FIG. 4, the combination of the material properties calculated from the spectral and from the non-spectral image data as a function of spatial frequency can be carried out in the spatial frequency domain. In this case the following relation may be used in order to obtain combined quantitative image data from the spectral and the non-spectral image data:

$$I_{enhanced} = \mathcal{F}^{-1}(w_{spectral}(f) \cdot \mathcal{F}(I_{spectral}(x)) + w_{non\text{-}spectral}(f) \cdot \mathcal{F}(I_{non\text{-}spectral}(x)))$$

$I_{enhanced}$ denotes the enhanced quantitative image data obtained from combining the spectral and non-spectral image data. Further, $I_{spectral}$ denotes the spectral image data and $I_{non\text{-}spectral}$ the non-spectral image. The functions $w_{spectral}$ and $w_{non\text{-}spectral}$ denote spatial-frequency dependent weighting functions and $\mathcal{F}$ and $\mathcal{F}^{-1}$ are the Fourier and inverse Fourier transforms, respectively. A weighting according to the above equation is mathematically equivalent to the following calculation in the spatial domain:

$$I_{enhanced} = v_{spectral}(x) * I_{spectral}(x) + v_{non\text{-}spectral}(x) * I_{non\text{-}spectral}(x)$$

In the latter case, $v_{spectral}(x) = \mathcal{F}^{-1}(w_{spectral}(f))$ and $v_{non\text{-}spectral}(x) = \mathcal{F}^{-1}(w_{non\text{-}spectral}(f))$ are filter kernels and * denotes the convolution operator. It is noted that the two aforementioned calculations are mathematically equivalent. Differences on the end result can be attributed to numerical precision and quality of the software implementation, and the choice of method might depend on practicalities such as speed of running the software. It should also be noted that other methods exist for processing images as a function of spatial frequency and structure size, for instance wavelet methods and Gaussian/Laplacian pyramid methods. The invention is not limited to any particular method of processing.

Figure 5A:
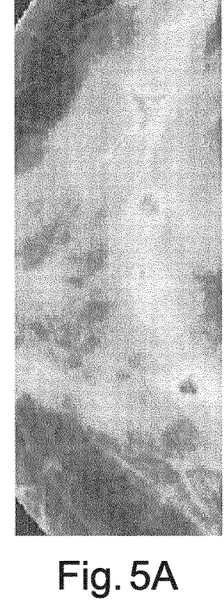
FIGS. 5A and 5B show the comparison of volumetric breast-density maps obtained without and with a method according to an embodiment of the invention.
Figure 5B:
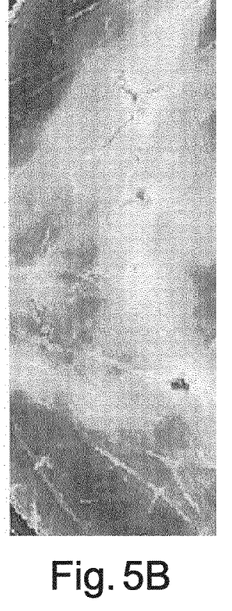

FIG. 5A and FIG. 5B illustrate advantages of the implementation of some of the embodiments described above. Both FIG. 5A and FIG. 5B show maps of volumetric breast density or glandularity, i.e. the fraction of glandular tissue thickness relative the total thickness on a pixel-by-pixel basis. In case of FIG. 5A, the a map of glandularity is shown, which has been calculated from spectral tomosynthesis data by decomposing the image into glandular and adipose thicknesses. Even though the map shows the overall structures well, the amount of detail is limited. In case of the calculations leading to the map in FIG. 5B, both spectral and non-spectral image data have been used and combined according to embodiments of the invention as described above. In particular, the non-spectral data were obtained by segmenting the tomosynthesis volume in 3D on a slice-by-slice basis in order to find the glandular structures and separate these from the adipose background. The segmentation worked well for small structures, but was not reliable for larger structures because of the limited depth resolution. The spectral and non-spectral image data were subsequently combined by weighting with spatial frequencies in such a way that the low-spatial-frequency parts of the spectral data and the high-spatial-frequency parts of the non-spectral image data received stronger weights according to the above described weighting step w. As compared to the image in FIG. 5A derived from spectral image data, the image in FIG. 5B obtained from a combination of spectral and non-spectral image data shows a higher level of detail without increased noise. The latter improved or enhanced image quality is one specific objective of the present invention. It is noted, for completeness, that the images in FIGS. 5A and 5B are processed with a large pixel size (0.4×0.4 mm).

While the present invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure and the dependent claims.

In the claims, the word "comprising" does not exclude other elements or steps, and the indefinite article "a" or "an" does not exclude a plurality. A single processor or other unit may fulfill the functions of several items re-cited in the claims. Any reference sign in the claims should not be construed as limiting the scope.

The invention claimed is:

1. An X-ray imaging system, comprising:
   an X-ray source configured to generate X-rays directed at an object of interest;
   an X-ray detector configured to acquire spectral and non-spectral image data of the object of interest;
   a receiving unit configured to receive the spectral and non-spectral image data of the object of interest; and
   a processor configured to:
      calculate material properties as a function of position from the spectral and non-spectral image data; and
      combine the material properties calculated from the spectral and non-spectral image data as a function of spatial frequency by weighting the spectral and non-spectral image data depending on the spatial frequencies in the image so as to generate a map of the material properties of the object of interest based on the weighted combination of the calculated material properties.

2. The X-ray imaging system according to claim 1,
   wherein the processor is configured to give stronger weight to the low-spatial-frequency parts of the spectral image data as compared to the low-spatial-frequency parts of the non-spectral image data; and
   wherein the processor is configured to give stronger weight to the high-spatial-frequency parts of the non-spectral image data as compared to the high-spatial-frequency parts of the spectral image data.

3. The X-ray imaging system according to claim 1, wherein the spectral image data and/or the non-spectral image data are phase contrast image data, differential phase contrast image data, or dark field image data.

4. A method for quantitative image data processing in an X-ray imaging system, the method comprising:
acquiring the spectral image data of the object of interest;
calculating material properties as a function of position from the spectral image data;
acquiring non-spectral image data of the object of interest;
calculating material properties as a function of position from the non-spectral image data; and
combining the material properties calculated from the spectral image data and the non-spectral image data as a function of spatial frequency by weighting the spectral image data and the non-spectral image data depending on the spatial frequencies of the image so as to generate a map of the material properties of the object of interest based on the weighted combination of the calculated material properties.

5. The method according to claim 4, wherein the spectral image data are spectral tomosynthesis data and/or the non-spectral image data are non-spectral tomosynthesis data.

6. The method according to claim 4, wherein acquiring the non-spectral image data comprises using additional a priori assumptions and/or additional data input.

7. The method according to claim 4, wherein combining the material properties calculated from the spectral image data and the non-spectral image data as a function of spatial frequency is at least partly carried out in the spatial-frequency domain.

8. The method according to claim 4, wherein combining the material properties calculated from the spectral image data and the non-spectral image data as a function of spatial frequency is at least partly carried out in the spatial domain and comprises a convolution with a filter kernel and/or low-pass, band-pass or high-pass filtering.

9. The method according to claim 4, wherein weighting as a function of spatial frequency gives stronger weight to the low-spatial-frequency parts of the spectral image data as compared to the low-spatial-frequency parts of the non-spectral image data, and wherein weighting as a function of spatial frequency gives stronger weight to the high-spatial-frequency parts of the non-spectral image data as compared to the high-spatial-frequency parts of the spectral image data.

10. The method according to claim 4, wherein calculating material properties as a function of position from the spectral image data and the non-spectral image data includes identifying or characterizing at least one of:
properties identifying a lesion, such as a cyst or a tumor or a microcalcification;
properties identifying glandular and adipose breast tissue or skin; and
concentration of a contrast agent inside the object of interest.

11. A non-transitory computer readable medium encoded with one or more executable instructions, which, when executed by at least ones processor, cause the at least one processor to perform a method for quantitative image data processing in an X-ray imaging system, the method comprising:
acquiring spectral image data of an object of interest;
calculating material properties as a function of position from the spectral image data;
acquiring non-spectral image data of the object of interest;
calculating material properties as a function of position from the non-spectral image data; and
combining the material properties calculated from the spectral image data and the non-spectral image data as a function of spatial frequency by weighting the spectral image data and the non-spectral image data depending on the spatial frequencies of the image data to create combined image data so as to generate a map of the material properties of the object of interest based on the weighted combination of the calculated material properties.

12. The non-transitory computer readable medium according to claim 11, wherein the spectral image data are spectral tomosynthesis data, and/or the non-spectral image data are non-spectral tomosynthesis data.

13. The non-transitory computer readable medium according to claim 11, further comprising employing additional a priori assumptions and/or additional data input.

14. The non-transitory computer readable medium according to claim 11, further comprising combining the material properties calculated from the spectral image data and the non-spectral image data as a function of spatial frequency at least in part in the spatial-frequency domain.

15. The non-transitory computer readable medium according to claim 11, further comprising combining the material properties calculated from the spectral image data and the non-spectral image data as a function of spatial frequency at least in part in the spatial domain using a convolution with a filter kernel.

16. The non-transitory computer readable medium according to claim 11, further comprising weighting as a function of spatial frequency to provide a stronger weight to the low-spatial-frequency parts of the spectral image data as compared to the low-spatial-frequency parts of the non-spectral image data, and weighting as a function of spatial frequency to provide a stronger weight to the high-spatial-frequency parts of the non-spectral image data as compared to the high-spatial-frequency parts of the spectral image data.

17. The non-transitory computer readable medium according to claim 11, further comprising calculating the material properties as a function of position from the spectral image data and the non-spectral image data by identifying or characterizing at least one of: properties identifying a lesion, properties identifying glandular and adipose breast tissue or skin, and concentration of a contrast agent inside the object of interest.

* * * * *